United States Patent [19]

Faubl

[11] 4,001,321
[45] Jan. 4, 1977

[54] PREPARATION OF α-6-DEOXYTETRACYCLINES
[75] Inventor: Hermann Faubl, Mystic, Conn.
[73] Assignee: Pfizer Inc., New York, N.Y.
[22] Filed: Oct. 22, 1975
[21] Appl. No.: 624,714

Related U.S. Application Data

[63] Continuation-in-part of Ser. No. 590,598, June 26, 1975, abandoned, which is a continuation-in-part of Ser. No. 534,452, Dec. 19, 1974, abandoned.

[52] U.S. Cl. .................................. 260/559 AT
[51] Int. Cl.² ................................. C07C 103/19
[58] Field of Search ......................... 260/559 AT

[56] References Cited
UNITED STATES PATENTS 3,165,551   1/1965   Blackwood et al. ........ 260/559 AT
3,200,149   8/1965   Blackwood et al. ........ 260/559 AT
3,794,671   2/1974   Wilkinson ..................... 252/431 P Primary Examiner—C. Davis
Attorney, Agent, or Firm—Connolly and Hutz

[57] ABSTRACT

Hydrogenation of a mixture prepared from a 6-deoxy-6-demethyl-6-methylenetetracycline compound, and a catalytic amount of a dicarboxylato(triphenylphosphine)rhodium(II) or dicarboxylato(substituted triphenylphosphine)rhodium(II) compound, in a reaction-inert solvent, produces the corresponding 6-deoxytetracycline compound. The hydrogenation takes place with a stereoselectivity which favors the 6α-isomer over the 6β-isomer. The products are known antibacterial agents.

17 Claims, No Drawings

PREPARATION OF α-6-DEOXYTETRACYCLINES

CROSS-REFERENCE TO RELATED APPLICATIONS

This application is a continuation-in-part of co-pending application Ser. No. 590,598 filed June 26, 1975 and now abandoned, which is a continuation-in-part of application Ser. No. 534,452 filed Dec. 19, 1974 and now abandoned.

BACKGROUND OF THE INVENTION

U.S. Patent 3,200,149 discloses the production of α-6-deoxytetracycline derivatives by a process which involves hydrogenation of certain 6-deoxy-6-demethyl-6-methylenetetracyclines in the presence of a catalytic amount of a noble metal catalyst such as rhodium or palladium. The process coproduces β-6-deoxytetracyclines, as well as α-6-deoxytetracyclines. One of the major objectives of the present invention was to improve upon that process so as to produce a higher α-isomer to β-isomer ratio.

It has now been found that a higher ratio of α-isomer to β-isomer can be achieved by hydrogenating a mixture prepared from the α-deoxy-6-demethyl-6-methylenetetracycline compound and a specific, soluble rhodium(II) species, in a reaction-inert solvent. The specific soluble rhodium(II) species is a dicarboxylato(triphenylphosphine)rhodium(II) or dicarboxylato(substituted triphenylphosphine)rhodium(II) species.

West German Offenlegungsschrift 2,308,227 broadly discloses the use of soluble rhodium species for the stereoselective reduction of 6-deoxy-6-demethyl-6-methylenetetracyclines. However, the said Offenlegungsschrift exemplifies only the use of rhodium(I) species. Hui et al., Inorganic Chemistry, 12, 757 (1973), and Journal of the Chemical Society (London), Part D, 1195 (1970), report that rhodium(II) diacetate is an effective hydrogenation catalyst. However, use of rhodium(II) diacetate in the process of the present invention does not lead to a favorable α to β ratio; approximately equal amounts of the α- and β- isomers are formed. The presence of the triphenylphosphine or substituted triphenylphosphine ligand is essential to obtain a stereoselective reduction. Although Legzdins et al., Journal of the Chemical Society (London), Part D, 825 (1969) have reported the use of rhodium diacetate in the presence of triphenylphosphine as a hydrogenation catalyst, their experiments were run in the presence of a very strong acid. The process of the present invention is carried out under neutral conditions, or on a weakly-acidic tetracycline acid-addition salt.

SUMMARY OF THE INVENTION

The present invention is based on the discovery that hydrogenation of a mixture prepared from a 6-deoxy-6-demethyl-6-methylenetetracycline and a specific rhodium species, in a reaction-inert solvent, results in hydrogenation of the exocyclic methylene group, and proceeds with a stereoselectivity which favors the β-isomers over the β-isomers by a factor of at least 9:1. The specific rhodium species used in the present invention is a compound of the formula:

wherein R is hydrogen, alkyl having from 1 to 6 carbon atoms, chloromethyl, dichloromethyl, trichloromethyl, fluoromethyl, difluoromethyl, trifluoromethyl, phenyl, chlorophenyl, tolyl or anisyl; and Q is triphenylphosphine or triphenylphosphine substituted on one or more of the phenyl rings by one or more substituents selected from the group consisting of alkyl having from 1 to 4 carbon atoms, alkoxy having from 1 to 4 carbon atoms, fluoro, chloro and bromo. However, the preferred catalysts are those wherein the triphenylphosphine group is unsubstituted. Especially preferred catalysts are those wherein the triphenylphosphine group is unsubstituted and R is alkyl, particularly methyl.

DETAILED DESCRIPTION OF THE INVENTION

The starting materials of the process of the present invention are selected from the group consisting of

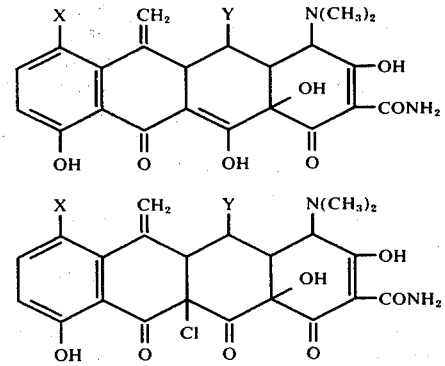

and the acid addition salts thereof;
wherein:
X is hydrogen or chloro; and
Y is hydrogen, hydroxy or alkanoyloxy having from 2 to 7 carbon atoms.

Preparation of these starting materials is fully disclosed and illustrated in U.S. Pat. No. 3,200,149. In general, the method of preparation involves treatment of a 11a-chloro-6,12-hemiketal of the appropriate tetracycline compound with a strong acid of the dehydrating type such as sulfuric, trifluoroacetic, polyphosphoric, perchloric, hydrogen fluoride and the like. Of these, the preferred is hydrogen fluoride. Optimum conditions are readily determined by routine experimentation. Generally, the selected 11a-chloroketal is merely added to the selected acid and allowed to react, most appropriately at a temperature within the range of from 0° to 50° C. and for a time of up to several hours. After reaction is complete, the product is recovered in an appropriate manner, e.g., in the case of volatile acids by evaporation of the same to obtain the residual product, and in other cases by standard procedure such as stirring with a non-solvent, e.g., diethyl ether, to precipitate the product. These 6-methylene compounds may be converted to acid addition salts or polyvalent metal salt complexes by standard procedures prior to hydrogenation.

When the desired starting material is an 11a-deschloro-6-deoxy-6-demethyl-6-methylenetetracycline, 11a-dechlorination may be accomplished by either chemical or catalytic reduction using procedures well known to those skilled in the art. Example XXXVII of U.S. Pat. No. 3,200,149 illustrates hydrogenation reduction of an 11a-chloro-6-deoxy-6-demethyl-6-methylenetetracycline hydrochloride to obtain the corresponding 11a-deschloro compound.

When Y of the starting materials for the present invention is alkanoyloxy having from 2 to 7 carbon atoms, it is appropriate to use the method of British Patent No. 1,287,493 for the preparation thereof. According to that method, the appropriate 11a-chloro-6-demethyl-6-deoxy-6-methylene-5-hydroxytetracycline in the form of the free base or a poly-addition salt is treated with a carboxylic acid having from 2 to 7 carbon atoms in the molecule in the presence of methanesulfonic, ethanesulfonic or hydrofluoric acid, preferably at a temperature of from 20° to 70° C. for a period of time generally ranging from 2 to 20 hours. The resulting product may then be reduced to the 11a-deschloro compound by the procedure described above.

The rhodium species of the formula $Rh(OCOR)_2Q$ are either known in the art, or they are simple analogs or homologs of compounds known in the art, and they can be prepared by methods such as those discussed by Stephenson et al., *Journal of the Chemical Society* (London), 3632 (1965). According to these procedures, rhodium carboxylates are prepared by refluxing rhodium hydrous oxide in, for example, an excess of formic, acetic or propionic acid and ethanol. The yellow solutions gradually turn amber and then green. The resulting solutions are cooled and the dark green powders which precipitate are filtered off and recrystallized from methanol or water. These products are found to be stable at temperatures up to 240° C. The final catalyst complex is prepared by the addition of triphenylphosphine, or the appropriately substituted triphenylphosphine, and diethyl ether to a cold ethanolic solution of the rhodium carboxylate.

Appropriate reaction inert solvents for the process of the present invention include those which serve to substantially dissolve the starting materials or the product. Examples of such solvents include ethers such as diethyl ether, tetrahydrofuran, dioxan, 1,2-dimethoxyethane; lower aliphatic ketones such as acetone and methyl ethyl ketone; low molecular weight esters such as ethyl acetate and butyl acetate; mono- and polyhydric lower alcohols such as methanol, ethanol, isopropanol, ethylene glycol, propylene glycol and diethylene glycol; lower alkoxy substituted alkanols such as 2-methoxyethanol and 2-(2-ethoxyethoxy)ethanol; lower alkanoic acids such as acetic acid and propionic acid; tertiary amides such as N,N-dimethylformamide, N,N-dimethylacetamide and N-methylpyrrolidone and mixtures thereof.

Introduction of the hydrogen gas into the reaction inert solvent medium containing the rhodium species and tetracycline is generally accomplished by carrying out the reaction in a sealed vessel under an atmosphere of hydrogen or of hydrogen mixed with an inert diluent such as nitrogen or argon. The pressure inside the reaction vessel may vary from about 1 to about 100 atmospheres. The preferred pressure range, when the atmosphere in the reaction vessel is substantially pure hydrogen, is from about 10 to about 100 psig.

The hydrogenation is generally run at a temperature of from about 20° to about 100° C., and preferably from about 40° to about 70° C. Utilizing the preferred temperature and pressure values, hydrogenation generally takes place in a few hours, e.g., from about 2 hours to about 10 hours.

On hydrogenating a 7-halo substituted 6-methylene-6-deoxy-6-demethyltetracycline starting material in the process of this invention, the 7-halo substituent remains substantially intact. On the other hand, an 11a-chloro substituent is removed.

The expression "catalytic amount" as used herein is well understood by those skilled in the art of known tetracycline hydrogenations. Generally, this amount ranges from about 0.1 to about 100 mol % based on the tetracycline substrate. The preferred amount is from about 1 to about 10 mol %.

The reaction product of the present invention may be isolated from the reaction medium by standard methods. For example, the product can often be induced to precipitate by the addition of a non-solvent such as hexane or water or by the addition of certain agents which form insoluble salts with the product. Alternatively, the crude product can be isolated by evaporation of the solvent or by dilution of the reaction mixture with a large excess of water followed by extraction of the product into a water-immiscible organic solvent and subsequent evaporation of the water-immiscible solvent.

The following examples are for the purpose of illustrating the present invention.

EXAMPLE 1

Reduction of 6-Methylene-6-demethyl-6-deoxy-5-hydroxytetracycline using Diacetato(triphenylphosphine)rhodium(II)

A solution of 2.0 g. (4.18 mmol) of 6-methylene-6-demethyl-6-deoxy-5-hydroxytetracycline hydrochloride and 0.088 g. (4.4 mol-percent) of diacetato(triphenylphosphine)rhodium(II) in 30 ml. of degassed methanol was shaken under an atmosphere of hydrogen, in a sealed vessel, at 60°–70° C., for 5.75 hours. The hydrogen pressure in the reaction vessel was 66–71 psig. The vessel was then opened and the reaction solution was filtered. The filtrate was examined by high-pressure liquid chromatography, which indicated that it contained the required α-6-deoxy-5-hydroxytetracycline, contaminated by 2–3% of its C-6 epimer.

To the filtrate was then added a mixture of 20 ml. of water and 30 ml. of 10% aqueous sulfosalicyclic acid, with stirring. Stirring was continued overnight, and then the precipitate was filtered off, giving 2.62 g. (95% yield) of α-6-deoxy-5-hydroxytetracycline as its sulfosalicyclate salt. The product was shown to be 93% pure by ultraviolet spectroscopy.

EXAMPLE 2

The procedure of Example 1 is repeated, except that the 6-methylene-6-demethyl-6-deoxy-5-hydroxytetracycline used therein is replaced by an equimolar amount of:

6-methylene-6-demethyl-6-deoxytetracycline,
6-methylene-6-demethyl-6-deoxy-5-acetoxytetracycline,
6-methylene-6-demethyl-6-deoxy-5-propionyloxytetracycline,
6-methylene-6-demethyl-6-deoxy-5-butyryloxytetracycline,
6-methylene-6-demethyl-6-deoxy-11a-chlorotetracycline,
6-methylene-6-demethyl-6-deoxy-5-hexanoyloxytetracycline,
6-methylene-6-demethyl-6-deoxy-7-chlorotetracycline,
6-methylene-6-demethyl-6-deoxy-7-chloro-5-hydroxytetracycline, 6-methylene-6-demethyl-6-deoxy-7-chloro-5-acetoxytetracycline,
6-methylene-6-demethyl-6-deoxy-7-chloro-5-isobutyryloxytetracycline,
6-methylene-6-demethyl-6-deoxy-7-chloro-5-isovaleroyloxytetracycline, and
6-methylene-6-demethyl-6-deoxy-7-chloro-5-heptanoyloxytetracycline, respectively,
and the diacetato(triphenylphosphine)rhodium(II) used therein is replaced by an equimolar amount of:
dipropionato(triphenylphosphine)rhodium(II),
dibenzoato(triphenylphosphine)rhodium(II),
dibutyrato(triphenylphosphine)rhodium(II),
di(p-chlorobenzoato) (triphenylphosphine)rhodium(II),
dibenzoato(triphenylphosphine)rhodium(II),
diformato(triphenylphosphine)rhodium(II),
diacetato(triphenylphosphine)rhodium(II),
dibenzoato(triphenylphosphine)rhodium(II),
di(m-toluato) (triphenylphosphine)rhodium(II),
dihexanoato(triphenylphosphine)rhodium(II),
diheptanoato(triphenylphosphine)rhodium(II), and
di(p-methoxybenzoato) (triphenylphosphine)rhodium(II),
respectively.
This affords the following compounds, respectively:
α-6-deoxytetracycline,
α-6-deoxy-5-acetoxytetracycline,
α-6-deoxy-5-propionyloxytetracycline,
α-6-deoxy-5-butyryloxytetracycline,
α-6-deoxytetracycline,
α-6-deoxy-5-hexanoyloxytetracycline,
α-6-deoxy-7-chlortetracycline,
α-6-deoxy-7-chloro-5-hydroxytetracycline,
α-6-deoxy-7-chloro-5-acetoxytetracycline,
α-6-deoxy-7-chloro-5-isobutyryloxytetracycline,
α-6-deoxy-7-chloro-5-isovaleroyloxytetracycline, and
α-6-deoxy-7-chloro-5-heptanoyloxytetracycline.

EXAMPLE 3

Rhodium(II) Acetate Dimer

A mixture of 1.72 g. of rhodium hydrous oxide (Rh[OH]$_3$.H$_2$O), 6 ml. of glacial acetic acid and 15 ml. of ethanol is heated under reflux for 24 hours. The reaction mixture is cooled, and the volatile components are removed by evaporation in vacuo to give the crude product. The crude product is purified by dissolving it in acetone, allowing the solvent to evaporate slowly and then filtering off the solid which precipitates.

EXAMPLE 4

Reaction of rhodium hydrous oxide with the appropriate carboxylic acid, according to the procedure of Example 3, produces the following rhodium(II) carboxylates:
rhodium(II) propionate,
rhodium(II) benzoate,
rhodium(II) butyrate,
rhodium(II) p-chlorobenzoate,
rhodium(II) formate,
rhodium(II) m-toluate,
rhodium(II) hexanoate,
rhodium(II) heptanoate,
rhodium(II) p-methoxybenzoate,
rhodium(II) chloroacetate,
rhodium(II) dichloroacetate,
rhodium(II) trichloroacetate,
rhodium(II) fluoroacetate,
rhodium(II) difluoroacetate, and
rhodium(II) trifluoroacetate.

EXAMPLE 5

Diacetato(triphenylphosphine)Rhodium(II)

A mixture of 110 mg. of rhodium(II) acetate dimer and 100 ml. of methanol is cooled to 17° C. and a solution of 131 mg. of triphenylphosphine in 5 ml. of ether is added with stirring. Stirring is continued at ambient temperature for 2 hours and then the precipitate is removed by filtration. This affords 219 mg. of the title compound, m.p. 203°–204° C.

EXAMPLE 6

The procedure of Example 5 is repeated, except that the rhodium(II) acetate dimer is replaced by the appropriate rhodium(II) carboxylate, to produce the following congeners:
dipropionato(triphenylphosphine)rhodium(II),
dibenzoato(triphenylphosphine)rhodium(II),
dibutyrato(triphenylphosphine)rhodium(II),
di(p-chlorobenzoato)(triphenylphosphine)rhodium(II),
diformato(triphenylphosphine)rhodium(II),
di(m-toluato)(triphenylphosphine)rhodium(II),
dihexanoato(triphenylphosphine)rhodium(II),
diheptanato(triphenylphosphine)rhodium(II),
di(p-methoxybenzoato)(triphenylphosphine)rhodium(II),
di(chloroacetato)(triphenylphosphine)rhodium(II),
di(dichloroacetato)(triphenylphosphine)rhodium(II),
di(trichloroacetato)(triphenylphosphine)rhodium(II),
di(fluoroacetato)(triphenylphosphine)rhodium(II),
di(difluoroacetato)(triphenylphosphine)rhodium(II), and
di(trifluoroacetato)(triphenylphosphine)rhodium(II).

EXAMPLE 7

Reduction of 6-Deoxy-6-demethyl-6-methylene-5-hydroxytetracycline using Rhodium(II) Diacetate A solution of 2.0 g. (4.18 mmol.) of 6-deoxy-6-demethyl-6-methylene-5-hydroxytetracycline hydrochloride and 46 mg. (5mol-percent) of rhodium(II) diacetate in 30 ml. of de-gassed methanol was shaken under an atmosphere of hydrogen at 65°–70° C. for 5.25 hours. The hydrogen pressure in the reaction vessel was 65-70 psig. The cooled reaction vessel was then opened and the contents were filtered. The filtrate was examined by high-pressure liquid chromatography. This indicated that it contained α-6-deoxy-5-hydroxytetracycline and β-6-deoxytetracycline, in a ratio of about 2:3, together with a small amount of unreduced starting material.

What is claimed is:

1. A process which comprises introducing a catalytic amount of a compound of the formula Rh(OCOR)$_2$(P[C$_6$H$_5$]$_3$) and a tetracycline compound selected from the group consisting of

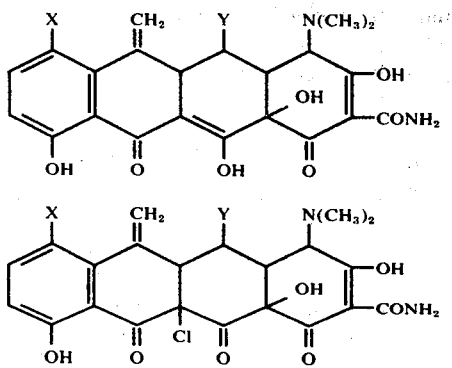

and the acid-addition salts thereof into a reaction-inert solvent, and maintaining hydrogen in contact with the reaction mixture thus formed, at a temperature of from about 20° to about 100° C., and at a pressure from about 1 to about 100 atmospheres until reaction of from about 1 to about 2 moles of hydrogen per mole of tetracycline compound occurs;

wherein R is selected from the group consisting of hydrogen, alkyl having from 1 to 6 carbon atoms, chloromethyl, dichloromethyl, trichloromethyl, fluoromethyl, difluromethyl, trifluoromethyl, phenyl, chlorophenyl, tolyl or anisyl;

X is selected from the group consisting of hydrogen and chloro;

and Y is selected from the group consisting of hydrogen, hydroxy and alkanoyl having from 2 to 7 carbon atoms.

2. The process according to claim 1, wherein the said tetracycline compound is selected from the group consisting of

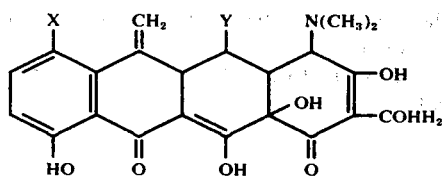

and the acid-addition salts thereof, wherein X is hydrogen and Y is hydroxy.

3. The process according to claim 2, wherein R is the said alkyl.

4. The process according to claim 3, wherein R is methyl.

5. The process according to claim 3, wherein said temperature is from about 40° to about 70° C.

6. The process of claim 3 wherein said catalytic amount is about 0.1 to about 100 mol-percent, based on said tetracycline compound.

7. The process of claim 3 wherein said catalytic amount is about 1 to about 10 mol-percent, based on said tetracycline compound.

8. The process of claim 3 wherein said reaction inert solvent medium is selected from the group consisting of diethyl ether, tetrahydrofuran, dioxan, 1,2-dimethoxy ethane, acetone, methyl ethyl ketone, ethyl acetate, butyl acetate, methanol, ethanol, isopropanol, ethylene glycol, propylene glycol, diethylene glycol, 2-methoxyethanol, 2-(2-ethoxyethoxy)-ethanol, acetic acid, propionic acid, N,N-dimethylformamide, N,N-dimethylacetamide, N-methylpyrrolidone, and mixtures thereof.

9. The process of claim 3 wherein said pressure is about 10 to about 100 psig.

10. The process according to claim 1, wherein said tetracycline compound is selected from the group consisting of

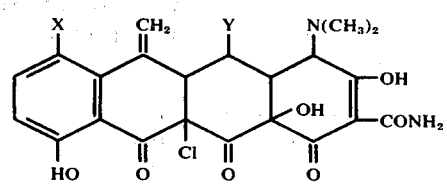

and the acid-addition salts thereof, wherein X is hydrogen and Y is hydroxy.

11. The process according to claim 10, wherein R is the said alkyl.

12. The process according to claim 11, wherein R is methyl.

13. The process according to claim 11, wherein said temperature is from about 40° to about 70° C.

14. The process of claim 11 wherein said catalytic amount is about 0.1 to about 100 mol-percent, based on said tetracycline compound.

15. The process of claim 11 wherein said catalytic amount is about 1 to about 10 mol-percent, based on said tetracycline compound.

16. The process of claim 11 wherein said reaction inert solvent medium is selected from the group consisting of diethyl ether, tetrahydrofuran, dioxan, 1,2-dimethoxy ethane, acetone, methyl ethyl ketone, ethyl acetate, butyl acetate, methanol, ethanol, isopropanol, ethylene glycol, propylene glycol, diethylene glycol, 2-methoxyethanol, 2-(2-ethoxyethoxy)ethanol, acetic acid, propionic acid, N,N-dimethylformamide, N,N-dimethylacetamide, N-methylpyrrolidone, and mixtures thereof.

17. The process according to claim 11, wherein said pressure is about 10 to about 100 psig.

* * * * *

UNITED STATES PATENT AND TRADEMARK OFFICE
CERTIFICATE OF CORRECTION

PATENT NO. : 4,001,321

DATED : JANUARY 4, 1977

INVENTOR(S) : HERMANN FAUBL

It is certified that error appears in the above–identified patent and that said Letters Patent are hereby corrected as shown below:

Col. 1, line 25, "α-deoxy" should read -- 6-deoxy --; line 61, "β" should read -- α --.

Col. 7, line 45, that portion of the formula reading "COHH$_2$" should read -- CONH$_2$ --.

Signed and Sealed this twelfth Day of July 1977

[SEAL]

Attest:

RUTH C. MASON
*Attesting Officer*

C. MARSHALL DANN
*Commissioner of Patents and Trademarks*